United States Patent
Hatzfeld et al.

(10) Patent No.: US 7,476,538 B2
(45) Date of Patent: Jan. 13, 2009

(54) METHOD FOR ENHANCING KERATINOCYTE STEM CELLS

(75) Inventors: Jacques Hatzfeld, Antony (FR); Nicolas Fortunel, Breuillet (FR); Antoinette Hatzfeld, Antony (FR)

(73) Assignees: Centre National de la Recherche Scientifique, Paris (FR); L'Oreal, Paris (FR)

( * ) Notice: Subject to any disclaimer, the term of this patent is extended or adjusted under 35 U.S.C. 154(b) by 273 days.

(21) Appl. No.: 10/494,275

(22) PCT Filed: Oct. 30, 2002

(86) PCT No.: PCT/FR02/03738

§ 371 (c)(1),
(2), (4) Date: Dec. 15, 2004

(87) PCT Pub. No.: WO03/038073

PCT Pub. Date: May 8, 2003

(65) Prior Publication Data

US 2005/0106723 A1 May 19, 2005

(30) Foreign Application Priority Data

Oct. 30, 2001 (FR) .................................. 01 14025

(51) Int. Cl.
*C12N 5/00* (2006.01)
(52) U.S. Cl. ...................... 435/325; 424/93.7
(58) Field of Classification Search ........................ None
See application file for complete search history.

(56) References Cited

U.S. PATENT DOCUMENTS 5,292,655 A * 3/1994 Wille, Jr. ...................... 435/384
5,521,295 A * 5/1996 Pacifici et al. ............... 536/23.4

FOREIGN PATENT DOCUMENTS

WO WO 99/47644 9/1999

OTHER PUBLICATIONS

Bajaj-Elliott M et al. 1998. Interactions between stromal cell-derived keratinocyte growth factor and epithelial transforming growth factor in immune-mediated crypt cell hyperplasia. J Clin Invest 102: 1473-1480.*

Epidermal growth factor receptor precursor (Receptor tyrosine-protein kinase ErbB-1) [online]. Retrieved from NCBI EntrezProtein database Jan. 30, 2007. Retrieved from the Internet: <URL: http://www.ncbi.nlm.nih.gov/entrez/viewer.fcgi?db=protein&val=2811086>.*
Keratinocyte growth factor receptor 2 isoform KGFR [*Homo sapiens*] [online]. Retrived from NCBI EntrezProtein database Jan. 30, 2007. Retrieved from the Internet: <URL: http://www.ncbi.nlm.nih.gov/entrez/viewer.fcgi?db=protein&val=15281415>.*
Jones PH. 1996. Isolation and characterization of human epidermal stem cells. Clin Sci 91: 141-146.*
Kaur P et al. 2000. Adhesive properties of human basal epidermal cells: an analysis of keratinocyte stem cells, transit amplifying cells, and postmitotic differentiating cells. J Invest Dermatol 114: 413-420.*
Maguire HC et al. 1989. Distribution of neu (c-erb-B2) protein in human skin. J Invest Dermatol 89: 786-790.*
Jones Philip H et al: "Stem cell patterning and fate in human epidermis." Cell, vol. 80, No. 1, 1995, pp. 83-93.
Tani Hiroaki et al: "Enrichment for murine keratinocyte stem cells based on cell surface phenotype." Proceedings of the National Academy of Sciences of the United States, vol. 97, No. 20, Sep. 26, 2000, pp. 10960-10965.
Peus Dominik et al: "EGF-receptor tyrosine kinase inhibition induces keratinocyte growth arrest and terminal differentiation." Journal of Investigative Dermatology, vol. 109, No. 6, Dec. 1997, pp. 751-756.
Yasumoto Shigeru et al: "Telomerase activity in normal human epithelial cells." Oncogene, vol. 13, No. 2, 1996, pp. 433-439.
Barrandon Y et al: "Cell Size as a Determinant of the Clone-Forming Ability of Human Keratinocytes" Proceedings of the National Academy of Sciences of the United States, vol. 82, No. 16, 1985, pp. 5390-5394.
Jensen Uffe B et al: "The spatial relationship between stem cells and their progeny in the basal layer of human epidermis: A new view based on whole-mount labelling and lineage analysis." Development (Cambridge), vol. 126, No. 11, Jun. 1999, pp. 2409-2418.

* cited by examiner

*Primary Examiner*—Lora E Barnhart
(74) *Attorney, Agent, or Firm*—Young & Thompson

(57) ABSTRACT

The enrichment of a population of keratinocyte stem cells (KSCs) from a preparation of keratinocytes and KSCs, includes pre-enrichment by contacting a sample of keratinocytes and KSCs with a collagen-coated culture plate for a sufficient time for KSCs to adhere, followed by washing away the non-adherent cells and recovering the adherent cells. The recovered adherent cells are sorted by their expression level of EGFR so that cells are recovered that have an expression level of EGFR of less than about 50% of the maximum level of EGFR expression, and the recovered cells have an expansion potential of at least $10^9$ after about 100 days in culture.

2 Claims, 9 Drawing Sheets

Adherent population (12 min. on collagen I)

Non-adherent population (12 min. on collagen I)

A

- Isotypic control
- Anti-EGF-R-PE

B

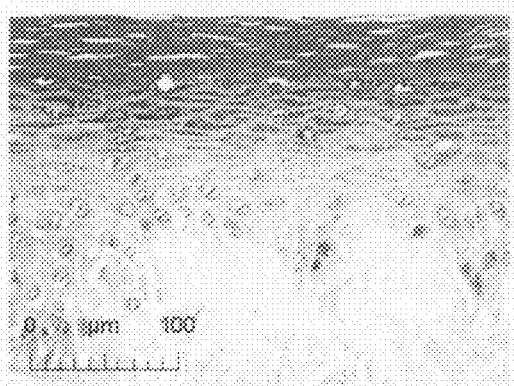
Figure 8A
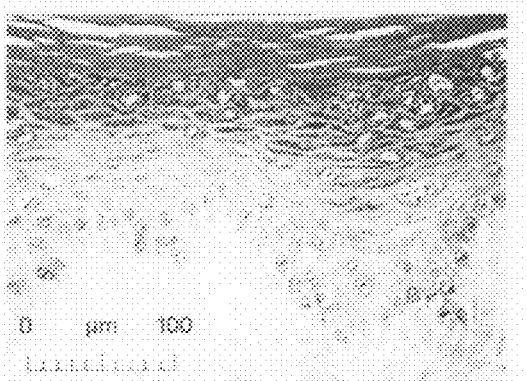
Figure 8B
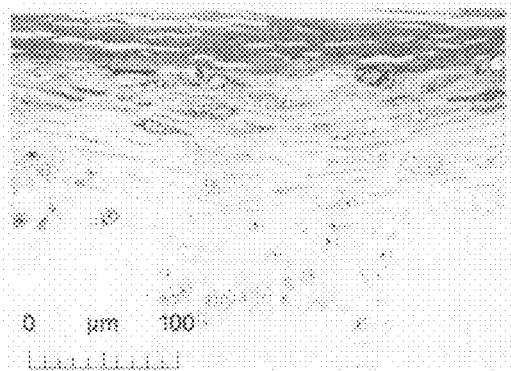
Figure 8C
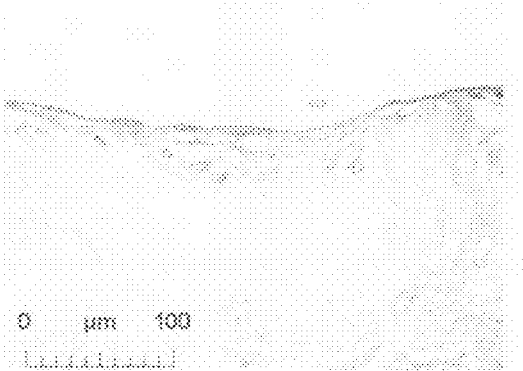
Figure 8D
Figure 8

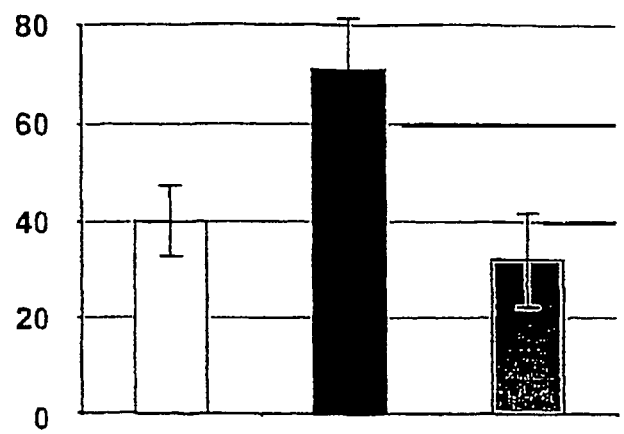
Figure 9A
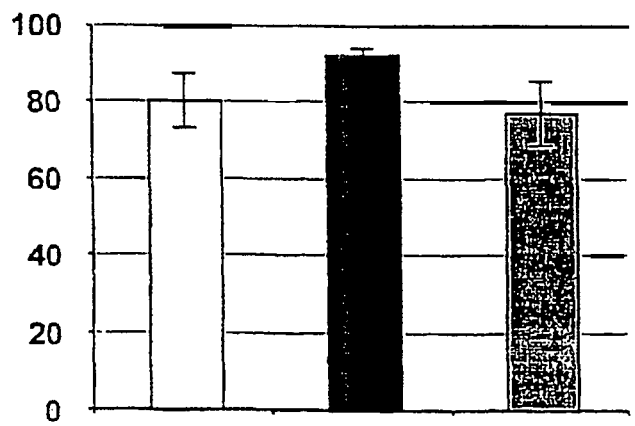
Figure 9B
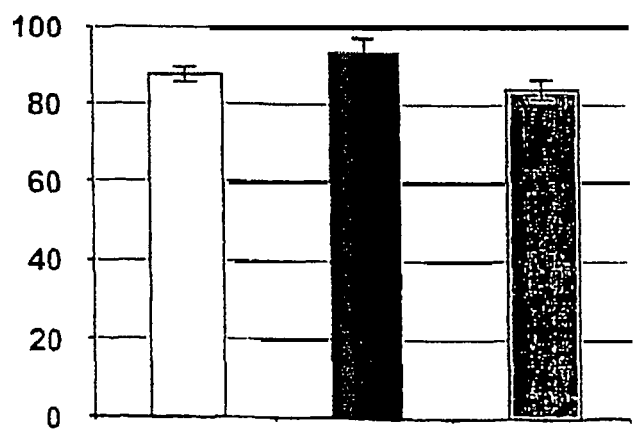
Figure 9C
Figure 9

METHOD FOR ENHANCING KERATINOCYTE STEM CELLS

BACKGROUND OF THE INVENTION

1. Field of the Invention

The invention pertains to a process for enriching keratinocyte stem cells.

The invention also pertains to keratinocyte stem cells having a high expansion potential.

2. Description of Related Art

Hematopoietic tissue and skin have similarities at the level of their organization. These are dynamic and hierarchized biological systems, in which large quantities of mature cells are continuously produced and renewed, throughout the life of the individual. The cells of which they are composed can be diagrammatically classified in 3 compartments according to their stage of evolution. However, there are no clearly defined boundaries between these compartments, each one of them being in reality constituted by a continuum of cells with a variable degree of maturation, and therefore very heterogeneous.

A first compartment is composed of differentiated mature cells the proliferation potential of which is very limited or nil (lymphocytes, macrophages, megacaryocytes, erythrocytes; keratinocytes of the suprabasal layers of the epidermis).

A second compartment includes a population of cells which have a variable but limited proliferation potential which they gradually lose by becoming committed towards differentiation (hematopoietic progenitors and precursors; keratinocytes in transitory amplification phase).

A third compartment is constituted by rare cells situated upstream in the hierarchy of these systems. It includes the stem cells (hematopoietic stem cell; keratinocyte stem cell) in particular characterized by the fact that, although mostly remaining in a state of quiescence, these cells have a very considerable long term expansion potential, but also in particular characterized by their self-renewal ability.

The phenotype of the keratinocyte stem cells having thus far been only imperfectly characterized, these cells remain at present difficult to purify, difficult to select, and consequently at present no effective process for enrichment of keratinocyte stem cells is available.

BRIEF SUMMARY OF THE INVENTION

One of the aims of the invention is to propose an effective process, making it possible to obtain a population of keratinocyte stem cells having a high long-term expansion potential.

One of the aims of the invention is to provide a population of keratinocyte stem cells having a proliferation potential at least approximately 100 times greater than the proliferation potential of the keratinocyte stem cells obtained by the standard processes.

A subject of the invention is more particularly a process for enriching a population of keratinocyte stem cells, from a preparation of keratinocytes, comprising a stage of pre-enrichment in keratinocyte stem cells by adhesion of said preparation to a component of extracellular matrices, in particular recognized by molecules involved in the adhesion of the keratinocytes, in particular by receptors of the integrin family, in particular collagen, for a duration of approximately 5 minutes to approximately 30 minutes, in particular approximately 10 minutes to approximately 20 minutes, advantageously 12 minutes, and the recovery of the stem cells having adhered to the abovementioned component of extracellular matrices by detachment under conditions allowing maintenance of the viability of the stem cells having adhered, in particular by trypsinization, in particular using 0.05% trypsin and 0.02% EDTA, in order to obtain a population of adherent cells.

By "population of keratinocyte stem cells" is meant a population of keratinocytes having a high long-term expansion potential, including clonogenic cells, and capable of reconstructing an epidermis.

By "preparation of keratinocytes", is meant all of the keratinocytes obtained from a skin sample or from other possible sources of stem cells capable of generating skin (for example hair follicles).

The adhesion is carried out by applying the preparation of keratinocytes to an adhesion substrate to which a component of extracellular matrices is adsorbed.

The cells which have not adhered to the adhesion substrate are eliminated by washing.

By "component of extracellular matrices", is meant in particular molecules such as the collagens, laminin, fibronectin, the proteoglycans (1 to 7).

The adhesion of the cells can be in particular verified by carrying out washings of the adhesion substrate under standard conditions. The adherent cells selected are not detached by this means.

If the adhesion duration is less than 5 minutes, the recovery yield is low, for example less than 1% relative to all of the cells contained in the preparation of keratinocytes.

If the adhesion duration is greater than 30 minutes, the separation is relatively indiscriminate, for example at least 30% of the cells contained in the preparation of keratinocytes are recovered.

The detachment takes place under conditions making it possible to maintain a good viability of the cells, i.e. to preserve all of the live cells (>97% of live cells after detachment).

The viability of the cells can in particular be determined by the method of exclusion with Trypan blue (8).

The process of the invention advantageously makes it possible to obtain a population of adherent cells having an expansion potential equal to or greater than approximately $10^9$.

The expression "population of adherent cells having an expansion potential greater than approximately $10^9$" means that the population in question can be amplified by a factor greater than approximately $10^9$ and therefore generate approximately $10^9$ times more cells than were used to initiate the cultures.

The expansion potential is estimated by the long-term use of cultures (more than 100 days) making it possible to establish a cumulative expansion curve (with reference to the culture procedure described hereafter in the examples).

According to an advantageous embodiment, in the enrichment process according to the invention, the percentage of adherent cells represents approximately 5% to approximately 20%, in particular approximately 10%, of the cells contained in the preparation of keratinocytes.

Another advantageous embodiment relates to a process for enriching a population of keratinocyte stem cells, from a preparation of keratinocytes, comprising a stage of pre-enrichment in keratinocyte stem cells by adhesion of said preparation to a component of extracellular matrices, in particular recognized by molecules involved in the adhesion of the keratinocytes, in particular by receptors of the integrin family, in particular collagen, for a duration of approximately 5 minutes to approximately 30 minutes, in particular approximately 10 minutes to approximately 20 minutes, advantageously 12 minutes, and the recovery of the stem cells having adhered to the abovementioned component of extracellular matrices by detachment under conditions making it possible to maintain the viability of the stem cells having adhered, in particular by trypsinization, in particular using 0.05% trypsin and 0.02% EDTA, in order to obtain a population of adherent cells, approximately 70% of the adherent cells expressing the α6 chain of the integrins.

The expression of the α6 chain of the integrins is in particular determined by immunophenotype marking and analyzed by flow cytometry.

According to an embodiment of the invention the adherent cells strongly express the α6 chain of the integrins.

The expression "strongly express the α6 chain of the integrins" means that the average fluorescence intensity is greater than 55 on day 1, according to data from a Becton Dickinson F.A.C.S. VANTAGE.

According to another advantageous embodiment, in the process according to the invention, the population of adherent cells comprises clonogenic cells, in particular at a level of at least approximately 1%, in particular at a level of at least 2% relative to the adherent cells.

By "clonogenic cells", is meant cells having the ability to produce a cell clone.

The character of clonogenicity of the cells can be verified by the implementation of a short-term culture test (from 6 to 12 days) (with reference to the culture procedure described hereafter in the examples).

The pre-enrichment stage of the process of the invention makes it possible to obtain clonogenic cells having an expansion potential equal to or greater than approximately $5 \times 10^{10}$.

The expression "clonogenic cells having an expansion potential equal to or greater than approximately $5 \times 10^{10}$" means that the clonogenic cells contained in the population of adherent cells have on average the ability to generate a filiation of at least approximately $5 \times 10^{10}$ keratinocytes.

Only the clonogenic cells effectively participate in the expansion. As indicated above, given that approximately 1% to 2% of the cells of the adherent population are clonogenic, the consequent expansion potential of these clonogenic cells is approximately 50 to 100 times greater than that estimated on the cell population scale.

According to another advantageous embodiment, the enrichment process according to the invention, comprises, after the pre-enrichment stage, a stage of enrichment by detection of the level of expression of a mitogenic receptor on the adherent cells and recovery of the fraction of adherent cells which represents approximately 20% to approximately 50% of the stem cells having the lowest level of expression of the mitogenic receptor, said expression being measured by flow cytometry, this fraction being designated "mitogenic receptor$^{low}$" fraction.

The stage of enrichment by detection of the level of expression of a mitogenic receptor makes it possible to separate the adherent cells into 2 fractions:
one fraction designated "mitogenic receptor$^{high}$" fraction which expresses the mitogenic receptor the most strongly and the other designated "mitogenic receptor-$^{low}$" fraction which contains 20% to 50% of the adherent cells expressing the mitogenic receptor the most weakly.

The results obtained have demonstrated in a reproducible manner that the most primitive keratinocytes which have the greatest expansion potential are significantly enriched in the mitogenic receptor$^{low}$ fraction.

By "mitogenic receptor", is meant a receptor capable of inducing entry into mitosis and therefore stimulating cell proliferation.

According to another advantageous embodiment, in the enrichment process according to the invention, the mitogenic receptor is chosen from the group comprising the receptors of growth factors capable of inducing the proliferation of keratinocyte stem cells and in particular the epidermal growth factor receptor (EGF-R), and the keratinocyte growth factor receptor (KGF-R).

By "receptor of growth factors capable of inducing the proliferation of keratinocyte stem cells", is meant any receptor the ligand of which is a growth factor capable of stimulating entry into mitosis and the proliferation of keratinocyte stem cells.

According to another embodiment, in the enrichment process according to the invention, the percentage of stem cells having the lowest level of expression of the mitogenic receptor is approximately 2% to approximately 5%, relative to the cells contained in the preparation of keratinocytes.

According to another embodiment, in the enrichment process according to the invention, the mitogenic receptor is EGF-R.

According to another embodiment, the enrichment process according to the invention comprises:
a stage of pre-enrichment in keratinocyte stem cells by adhesion on collagen, for a duration of approximately 10 minutes to approximately 20 minutes, in particular 12 minutes, the recovery of the cells having adhered to the collagen being carried out by detachment using trypsinization, using 0.05% trypsin and 0.02% EDTA in order to obtain a population of adherent cells,
a stage of enrichment by detection of the level of expression of the EGF-R receptor on the adherent cells obtained in the preceding stage, and the recovery of the fraction of stem cells which represents approximately 20% to approximately 50% of the adherent cells having the lowest level of expression of EGF-R, this fraction being designated EGF-R$^{low}$.

According to another embodiment, the enrichment process according to the invention comprises:
a stage of pre-enrichment in keratinocyte stem cells by adhesion on collagen, for a duration of approximately 10 minutes to approximately 20 minutes, in particular 12 minutes, the recovery of the cells having adhered to the collagen being carried out by detachment using trypsinization, using 0.05% trypsin and 0.02% EDTA in order to obtain a population of adherent cells, approximately 70% of said adherent cells expressing the α6 chain of the integrins,
a stage of enrichment by detection of the level of expression of the EGF-R receptor on the adherent cells obtained in the preceding stage, and the recovery of the fraction of stem cells which represents approximately 20% to approximately 50% of the adherent cells having the lowest level of expression of EGF-R, this fraction being designated by EGF-R$^{low}$.

According to another embodiment, the enrichment process according to the invention comprises:
a stage of pre-enrichment in keratinocyte stem cells by adhesion of a preparation of keratinocytes on a component of extracellular matrices, in particular recognized by molecules involved in the adhesion of keratinocytes, in particular by receptors of the integrin family, in particular collagen, for a duration of approximately 10 minutes to approximately 20 minutes, in particular 12 minutes, the recovery of the cells having adhered to the collagen being carried out by detachment using trypsinization, using 0.05% trypsin and 0.02% EDTA in order to obtain a population of adherent cells, approximately 70% of said adherent cells expressing the (α6 chain of the integrins, a stage of enrichment by detection of the level of expression of the EGF-R receptor on the adherent cells obtained in the preceding stage, and the recovery of the fraction of stem cells which represents approximately 20% to approximately 50% of the adherent cells having the lowest level of expression of EGF-R, this fraction being designated by EGF-R$^{low}$.

In the enrichment process according to the invention, the EGF-R$^{low}$ fraction has an expansion potential equal to or greater than approximately $10^{10}$.

The expression "EGF-R$^{low}$ fraction has an expansion potential equal to or greater than approximately $10^{10}$" means that the population of adherent cells can be amplified by a factor greater than approximately $10^{10}$ and therefore generate approximately $10^{10}$ times more cells than were used to initiate the cultures.

The expansion potential is estimated by the use of long-term cultures making it possible to establish a cumulative expansion curve (with reference to the culture procedure described hereafter in the examples).

According to an advantageous embodiment, in the enrichment process according to the invention, the EGF-R$^{low}$ fraction comprises clonogenic cells, in particular at least approximately 1% and in particular at least approximately 2% relative to the cells contained in the EGF-R$^{low}$ fraction.

The process according to the invention makes it possible to obtain clonogenic cells having an expansion potential equal to or greater than approximately $5\times10^{11}$.

The expression "clonogenic cells having an expansion potential equal to or greater than approximately $5\times10^{11}$" means that the clonogenic cells contained in the EGF-R$^{low}$ population of adherent cells have on average the ability to generate a filiation of at least approximately $5\times10^{11}$ keratinocytes.

Approximately 1% to 2% of the cells of the EGF-R$^{low}$ fraction are clonogenic, and consequently the expansion potential of these cells is approximately 50 to 100 times greater than that estimated on the cell fraction scale.

The invention also relates to a process for the culture of keratinocyte stem cells comprising culture of the "mitogenic receptor$^{low}$" fraction obtained according to the process defined above, with a seeding density of approximately 2,500 to approximately 7,000 cells/cm$^2$, in order to obtain at most approximately 120,000 cells/cm$^2$, followed by a detachment under conditions allowing the detachment of the cells under conditions which do not alter their viability, and by a subculture, the successive detachment and subculture stages taking place when the cell density reaches at most approximately 120,000 cells/cm$^2$.

The seeding density must be such that the cell expansion obtained between 2 successive subcultures is the highest possible, i.e. the number of cells can for example be multiplied by approximately at least 15 when the keratinocytes are in exponential growth phase (cell expansion greater than approximately 15).

If the seeding density is below 2,500 cells/cm$^2$ or if it is above 7,000 cells/cm$^2$, the cell expansion obtained between 2 successive subcultures (when the cells are in exponential growth phase) is below 15 and therefore not optimal.

The cells are detached when the number of cells obtained is approximately 120,000 cells/cm$^2$ in order to avoid the cultures reaching a state of confluence, such a state leading to a commitment of the cells to differentiation and leading to a halt in proliferation.

Following the detachment, a subculture is carried out of the cultures which are reseeded at a density comprised between approximately 2,500 and 7,000 cells/cm$^2$.

The successive detachment and subculture stages are carried out when the cell density reaches at most approximately 120,000 cells/cm$^2$.

The culture process is stopped when the expansion potential of the cell population tested is exhausted: the culture enters into a state of senescence and spontaneously ceases to proliferate.

According to an advantageous embodiment, in the process for culturing keratinocyte stem cells according to the invention, the detachment stage takes place under conditions allowing on the one hand the detachment of some of the cells which are easiest to detach, for example using 0.05% trypsin+0.02% EDTA and on the other hand the detachment of cells which are most difficult to detach, for example using 0.25% trypsin+0.02% EDTA.

According to another advantageous embodiment, the process for culturing keratinocyte stem cells comprises the culture of the EGF-R$^{low}$ fraction defined above, with a seeding density of approximately 2,500 to approximately 7,000 cells/cm$^2$ in order to obtain at most approximately 120,000 cells/cm$^2$, followed by detachment under conditions allowing the detachment of some of the cells which are easiest to detach, using 0.05% trypsin+0.02% EDTA and the detachment of the cells which are most difficult to detach using 0.25% trypsin+0.02% EDTA, and followed by the subculture of the stem cells obtained.

The invention relates to a composition of stem cells as obtained by implementation of the pre-enrichment stage as defined above.

The invention also relates to a composition of stem cells as obtained by implementation of the process according to the invention The invention also relates to a composition of keratinocyte stem cells comprising keratinocyte stem cells (KSCs), having an expansion potential equal to or greater than $10^{10}$.

The invention also relates to a KSC composition as defined above, in which the KSCs are viable.

The invention also relates to a stem cells composition as defined above, containing KSCs on the surface, the level of expression of a mitogenic receptor of which is weak, the qualifier "low" being defined relative to the profile of expression of the mitogenic receptor observed in said KSC composition.

The invention relates to a composition of stem cells as defined above, in which the level of expression of the EGF receptor (EGF-R) is low.

The invention relates to the use of a composition of keratinocyte stem cells as defined above, for the reconstruction of skin.

BRIEF DESCRIPTION OF THE DRAWING FIGURES

FIGS. 8A, 8B, 8C and 8D show the ability of Adh$^{+++}$EGF-$R^{low}$ primitive cells to generate in vitro a pluristratified epidermis.

FIGS. 9A, 9B and 9C show phenotyping by flow cytometry of the non-fractionated population of keratinocytes and of the adherent and non-adherent fractions obtained after pre-enrichment.

DETAILED DESCRIPTION OF THE PREFERRED EMBODIMENTS

A detailed embodiment of the invention is described hereafter.

I/Pre-Selection of a Cell Population of "Adherent" Cells, which Represents 10% of the Total Keratinocytes and Essentially Includes the KSCs.

1—Selection of cells from the population of "adherent" cells: The selection method is based on the adhesion ability of keratinocytes. The adhesion substrate chosen is a plastic support on which type I collagen is adsorbed. The preparations of keratinocytes originating from cutaneous samples is applied to the adhesion substrate, followed by incubation at 37° C. for a short time. The cells which have not adhered to the support are sampled, then the adherent cells are detached by mild trypsinization and recovered separately. It has been determined that an incubation duration of 12 minutes is suitable for the selection of a population enriched with cells capable of initiating a cell expansion in vitro. The cells having adhered are designated "adherent".

2—Phenotypical characteristics of cells of the population of "adherent" cell: Analyses of the expression of surface molecules involved in cell adhesion were carried out by flow cytometry on the non-fractionated population, as well as on the population of adherent cells and the population of non-adherent cells (FIG. 9). It was observed that the population of adherent cells is significantly enriched with cells expressing the α6 chain of the integrins (CD49f) (approximately 70% of the cells have the α6 integrin at their surface), a criterion associated with the most primitive keratinocytes, whilst the population of non-adherent cells is less rich in this (approximately 30% of the cells have the α6 integrin at their surface). An expression of the α2 and β1 chains of the integrins is detected in a less specific manner at the surface of the cells originating from the total (non-fractionated), adherent, and non-adherent populations.

Figure 1:
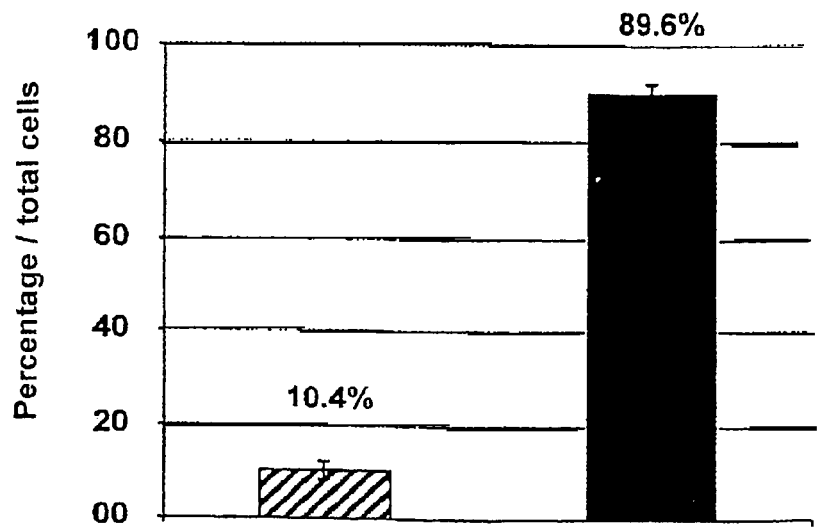
FIGS. 1A and 1B show the enrichment of clonogenic cells obtained after selection by the method of adhesion on type I collagen.
Figure 1:
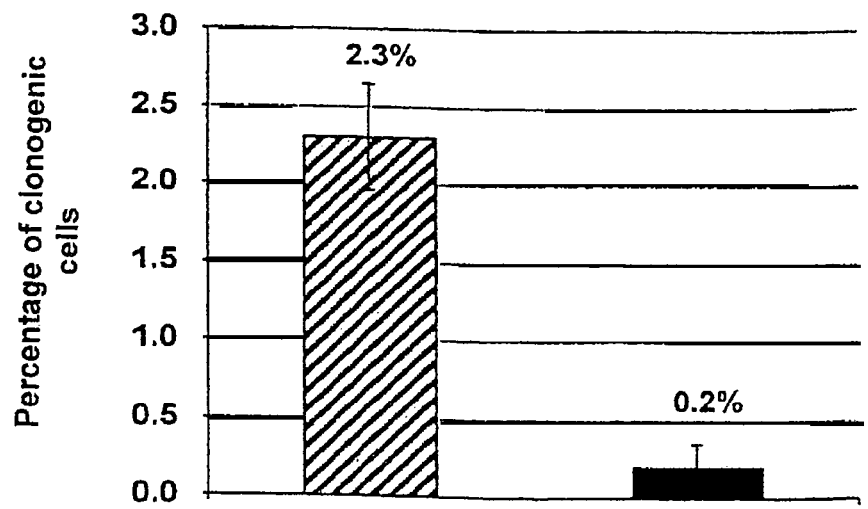
Figure 1:
Figure 1:

3—Functional characteristics of the cells of the population of "adherent" cells: Statistical analysis carried out on several independent samples (n>5 experiments) shows that the population of adherent cells represents only 10.4% of the total keratinocytes, but has a considerable enrichment with clonogenic cells (FIG. 1A). In fact, the realization of short-term clonogenic tests (6 days) on these two cell populations indicates that 2.3% of the keratinocytes originating from the population of non-adherent cells over 12 minutes have the ability to generate clones on a plastic support whilst only 0.2% of the cells of the population of non-adherent cells are clonogenic (FIG. 1B).

Figure 2:
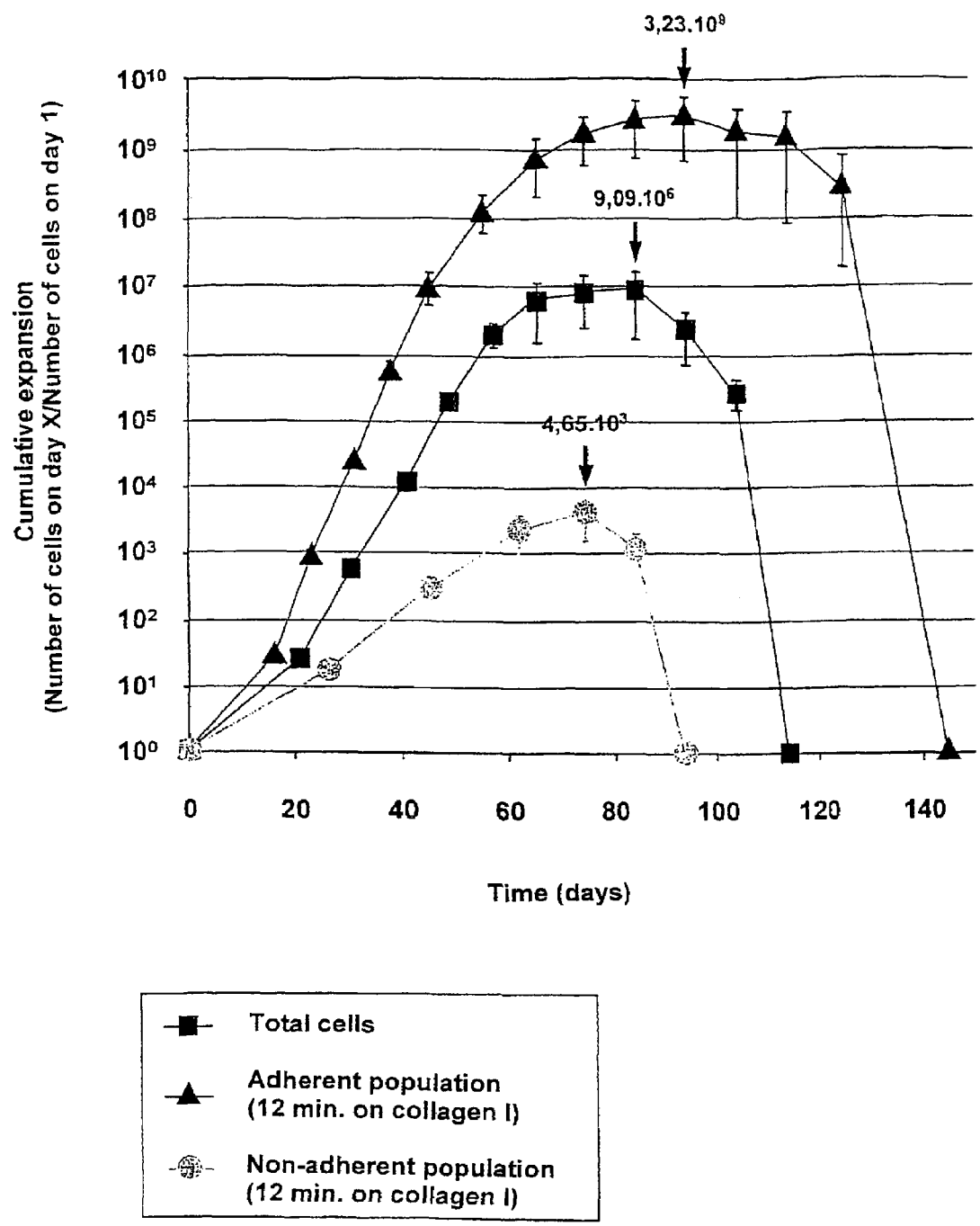
FIG. 2 shows the comparison of the expansion potential of the keratinocytes contained in the non-fractionated population, with the adherent and non-adherent cell populations.

The content of each one of the populations of cells selected by the method of rapid adhesion on type I collagen in keratinocytes having a strong expansion potential, a property more representative of the physiological function of the KSCs, was evaluated. The results obtained from several independent samples (n>5 experiments) show that the most primitive cells, which express the strongest long-term proliferation potential, are enriched in the population of adherent cells (FIG. 2). In fact, the cells contained in this population make it possible to obtain a cumulative expansion greater than that of the total population. On the other hand, the population of non-adherent cells appears to be mostly constituted by later keratinocytes, and expresses only a lower proliferation potential.

II/Screening of a Fraction of Cells Called "Adherent EGF-$R^{low}$" which Represents 20% to 45% of the Cells of the Population of "Adherent" Cells, therefore 2% to 4.5% of the Total Keratinocytes, and Essentially Includes KSCs.

Figure 3:
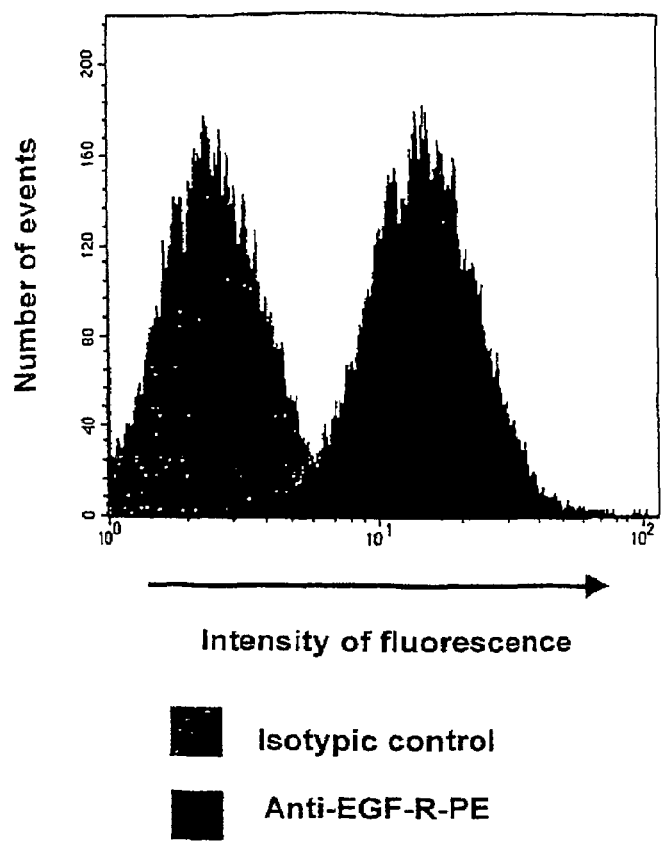
FIGS. 3A and 3B show the separation of the population of the keratinocytes of adherent cells into two fractions on the basis of the level of expression of the EGF-R.
Figure 3:
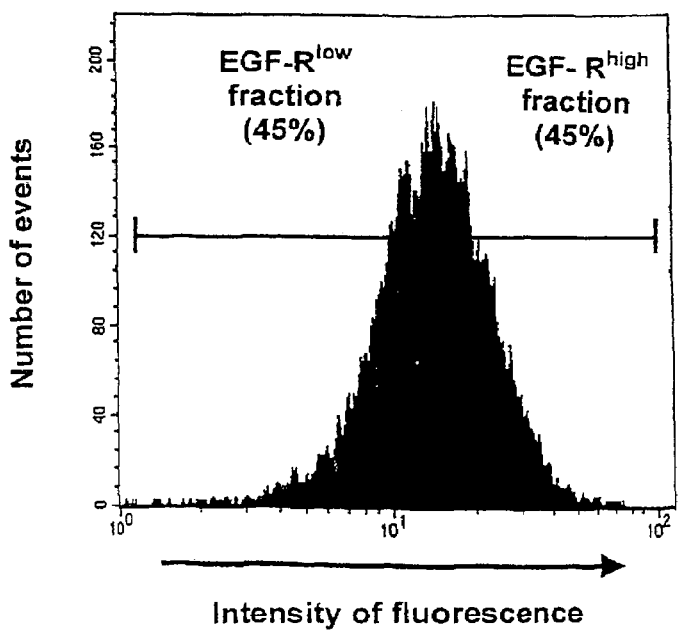
Figure 4:
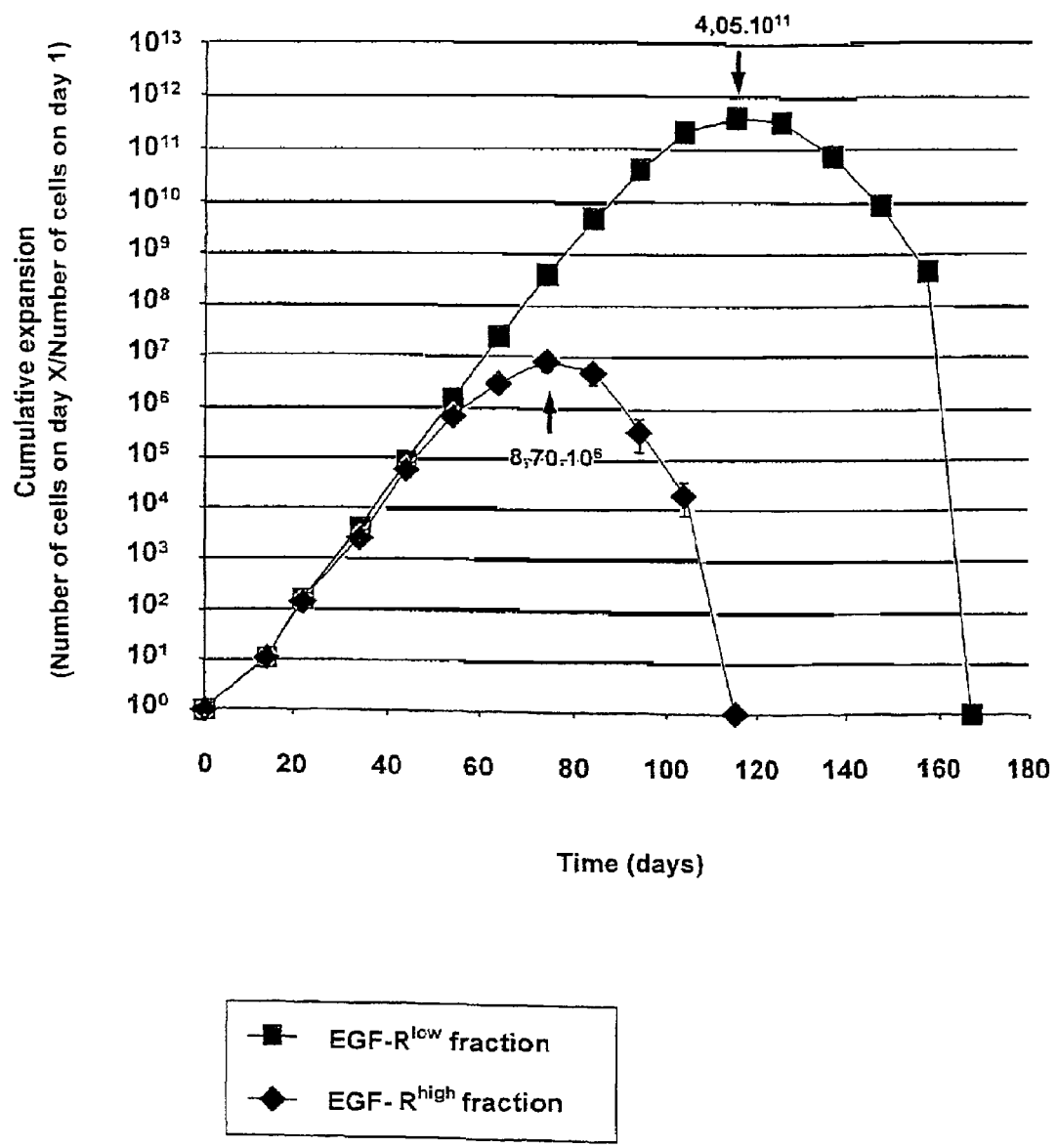
FIG. 4 shows a comparison of the longterm expansion potential of the keratinocytes contained in the "EGF-R$^{low}$" and "EGF-R$^{high}$" phenotype fractions.
Figure 5:
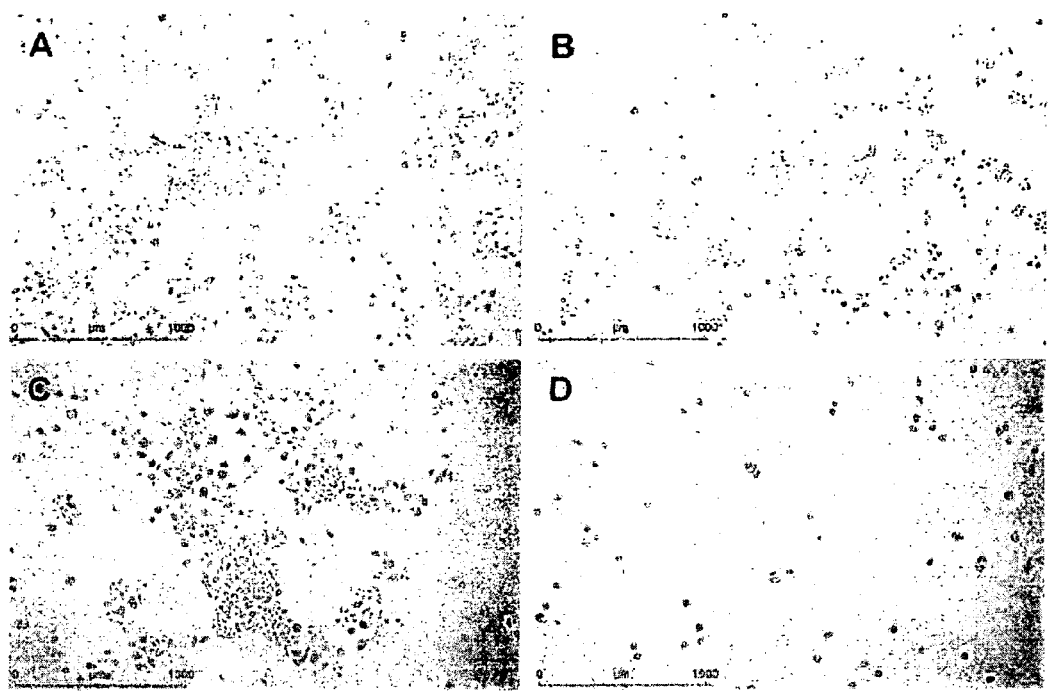
FIGS. 5A, 5B, 5C and 5D show cultures originating from the EGF-R$^{low}$ and EGF-R$^{high}$ fractions.

1—Fraction of cells composed of 45% of the cells of the "adherent" cell ponulation most weakly expressing the EGF-R: The population composed of the adherent cells over 12 minutes on type I collagen was firstly separated into 2 fractions of equivalent size on the basis of the level of expression of the EGF-R detectable at their surface. The fraction qualified as "EGF-$R^{low}$" contains 45% of the adherent keratinocytes most weakly expressing the EGF-R and the fraction qualified as "EGF-$R^{high}$" contains 45% of the adherent keratinocytes most strongly expressing this receptor (FIG. 3). These experiments were carried out on several independent samples (n>5). The results obtained demonstrate in a reproducible manner that the most primitive keratinocytes which have the greatest expansion potential are significantly enriched in the EGF-$R^{low}$ fraction (FIG. 4). This correlates with the microscopic observation of the cells at different culture times, which reveals a production of keratinocytes which are small in size, non-differentiated in the longer term in the cultures initiated from the EGF-$R^{low}$ fraction (FIG. 5), a criterion associated with the primitive keratinocytes (9).

2—Fraction composed of 20% of the cells of the population of "adherent" cells most weakly expressing the EGF-R: The population of adherent cells was finally separated into 4 fractions of equivalent size on the basis of the level of expression of the EGF-R detectable at the surface of the cells.

Four fractions of equal representativity and each comprising 20% of the cells of this population were defined as "EGF-$R^{-/+}$", "EGF-$R^{++}$", "EGF-$R^{+++}$", and "EGF-$R^{++++}$" fractions (FIG. 6): the fractions called "EGF-$R^{-/+}$" and "EGF-$R^{++}$" are included in the EGF-$R^{low}$ fraction and each contain 20% of the cells of the adherent population; the fractions called "EGF-$R^{+++}$" and "EGF-$R^{++++}$" are included in the EGF-$R^{high}$ fraction and each contain 20% of the cells of the adherent population. An inverse proportionality was observed between the level of expression of the EGF-R at the surface of the cells thus selected, and their long-term proliferation potential (FIG. 7). In fact, the greatest cumulative expansion is obtained from the EGF-$R^{-/+}$ fraction whilst the value obtained from the EGF-$R^{++++}$ fraction proves to be the lowest. The EGF-$R^{++}$ and EGF-$R^{+++}$ fractions behave in intermediate manner (n>3 independent experiments carried out).

These experimental results validate the possibility of using a mitogenic growth factor receptor (EGF tyrosine kinase receptor) as a phenotypical marker in order to select a fraction of keratinocytes significantly enriched in KSCs.

III/Optimal Evaluation of the Long-term Expansion Potential of the Populations of Selected Keratinocytes.

1—Controlled trypsinization of the cells during successive subcultures: The objective is to limit the stress caused to the cells during the successive detachments and subcultures of the long-term cultures, a problem which could lead to an underestimation of their potential. Firstly a controlled proteolytic treatment is carried out (0.05% trypsin-0.02% EDTA) which allows the detachment of some of the cells whilst avoiding subjecting them to too drastic a proteolytic treatment which could alter their viability. The cells most difficult to detach for which mild proteolysis has proved ineffective are then subjected to a stronger proteolytic treatment (0.25% trypsin-0.02% EDTA), which finally makes it possible to recover all of the population. A comparative study of the impact of different detachment methods on the viability of the cells was carried out.

2—Seeding density of the culture flasks suitable for optimal expansion of the keratinocytes: In order to evaluate which seeding densities are compatible with a good demonstration of the expansion potential of the cells tested, during the initiation of the long-term cultures as well as at each successive subculture, experiments were carried out over a 7-day period. These made it possible to determine that seeding densities comprised between 2500 and 7000 cells/cm$^2$ are the most suitable since they make it possible to obtain a cell expansion by a factor of 15 to 20, whilst lower and higher seeding densities produce poorer results.

FIGS. 1A and 1B: Representativity and clonogenicity of the cell populations of "adherent" cells and "non-adherent" cells.

FIGS. 1A and 1B show the enrichment in clonogenic cells obtained after selection by the method of adhesion on type I collagen.

The total keratinocytes isolated from a skin sample were separated into a cell population called "adherent" and a population called "non-adherent" by a 12-minute stage of adhesion on type I collagen. The representativity of each fraction relative to the total cell population was evaluated, as well as their clonogenic keratinocytes content.

FIG. 1A shows the percentage of cells constituting the population of adherent cells relative to the total cells (hatched column) and the percentage of cells constituting the population of non-adherent cells relative to the total cells (filled-in column).

FIG. 1B shows the percentage of clonogenic cells respectively in the population of adherent cells (hatched column) and in the population of adherent cells (filled-in column).

The results obtained show that the cell population called "adherent" is significantly enriched in clonogenic cells, since it represents only 10% of the total keratinocytes but contains a percentage of clonogenic cells 10 times higher than that of the population called "non-adherent".

FIG. 2: Comparison of the expansion potential of the keratinocytes contained in the non-fractionated population, with the "adherent" and "non-adherent" cell populations.

The total keratinocytes isolated from a skin sample were separated into a cell population called "adherent" and a population called "non-adherent" by a 12-minute stage of adhesion on type I collagen. The cells contained in the 2 populations, as well as those of the total non-fractionated population, were subjected to a long-term culture test (cumulative total number of cells produced), in order to compare their expansion potential.

The x-axis represents time (expressed in number of days) and the y-axis the cumulative expansion (number of cells produced on day X/number of cells on day 1).

The curve with black squares corresponds to the results obtained from the cells of the total population, those with triangles from the cells of the adherent population (12 minutes on collagen I) and those with circles from the cells of the non-adherent population (12 minutes on collagen I).

The results obtained show that the cell population called "adherent" essentially contains primitive cells with a strong expansion potential, whilst the cell population called "non-adherent" is mostly composed of later keratinocytes which only express a reduced potential expansion.

FIGS. 3A and 3B: Separation of the population of keratinocytes of "adherent" cells into 2 fractions on the basis of the level of expression of the EGF-R.

Keratinocytes of the "adherent" fraction, pre-enriched in primitive cells by a stage of adhesion on type I collagen, were marked by a fluorescent antibody directed against the EGF-R (antibody directed against the EGF-R extracellular domain). The signal was analyzed in semi-quantitative manner by flow cytometry.

FIG. 3A shows a marking profile representative of the EGF-R obtained from keratinocytes of the adherent fraction (darker surface), as well as the corresponding control profile (lighter surface). The x-axis represents the intensity of fluorescence measured by flow cytometry and expressed on a logarithmic scale. The y-axis represents the distribution of the cells analyzed as a function of the intensity of the fluorescent signal measured.

FIG. 3B makes it possible to visualize the Gaussian distribution of the level of expression of the EGF-R at the surface of the keratinocytes of the adherent fraction (x and y-axes identical to those of FIG. 3A). The results obtained show a distribution of the signal sufficiently spread-out to allow the screening of cells either expressing the EGF-R weakly, or expressing this receptor strongly. The profile presented illustrates a separation of the adherent population into 2 fractions: the one, called "EGF-R$^{low}$", contains 45% of the adherent cells expressing the lower level of EGF-R at their surface; the other, called "EGF-R$^{high}$", contains 45% of the adherent cells which express the stronger level of EGF-R at their surface.

FIG. 4: Comparison of the long-term expansion potential of the keratinocytes contained in the "EGF-R$^{low}$" and "EGF-R$^{high}$" phenotype fractions.

The total keratinocytes isolated from a skin sample were pre-enriched in primitive cells by the method of adhesion on type I collagen, then separated into 2 fractions: the one, called "EGF-R$^{low}$", contains 45% of the adherent cells expressing the lowest level of EGF-R at their surface; the other, called "EGF-R$^{high}$", contains 45% of the adherent cells which express the highest level of EGF-R at their surface. The long-term expansion potential (cumulative total number of cells produced) of these 2 fractions was compared.

The x-axis corresponds to the culture time expressed in days and the y-axis to the cumulative expansion already defined.

The curve with black squares corresponds to the results obtained from the cells of the EGF-R$^{low}$ fraction and that with diamonds to those obtained from the cells of the EGF-R$^{high}$ fraction.

The results obtained show that the cell fraction called "EGF-R$^{low}$" essentially contains primitive cells with a high expansion potential, whilst the cells of the cell fraction called "EGF-R$^{high}$" have a lower expansion potential.

FIGS. 5A, 5B, 5C and 5D: Cultures originating from the "EGF-R$^{low}$" and "EGF-R$^{high}$" fractions.

FIG. 5A corresponds to a culture originating from the EGF-R$^{low}$ fraction (Day 34 of culture)

FIG. 5B corresponds to a culture originating from the EGF-R$^{high}$ fraction (Day 34 of culture)

FIG. 5C corresponds to a culture originating from the EGF-R$^{low}$ fraction (Day 70 of culture)

FIG. 5D corresponds to a culture originating from the EGF-R$^{high}$ fraction (Day 70 of culture)

The total keratinocytes isolated from a skin sample were pre-enriched in primitive cells by the method of adhesion on type I collagen, then separated into two fractions: the one, called "EGF-R$^{low}$", contains 45% of the adherent cells expressing the lowest level of EGF-R at their surface; the other, called "EGF-R$^{high}$", contains 45% of the adherent cells which express the highest level of EGF-R at their surface. The production of cells which are small in size, a criterion associated with the KSCs, was monitored over time by microscopic observation in the cultures originating from each of these 2 fractions.

The results obtained show that the cell fraction called "EGF-R$^{low}$" ensures a more prolonged production of primitive cells which are small in size than the cell fraction called "EGF-R$^{high}$".

Figure 6:
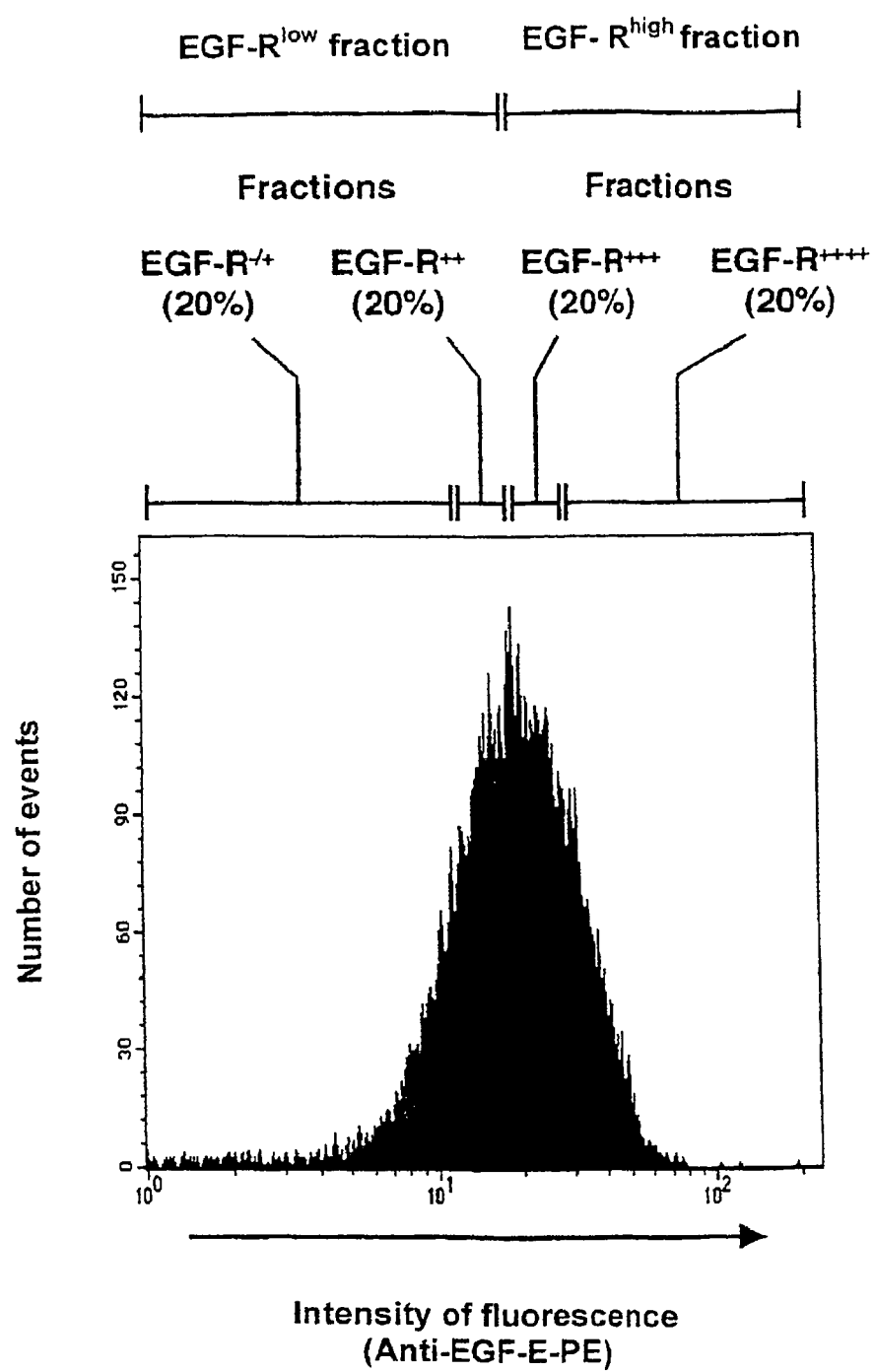
FIG. 6 shows a separation of the population of adherent keratinocytes into four fractions on the basis of the level of expression of the EGF-R.
Figure 7:
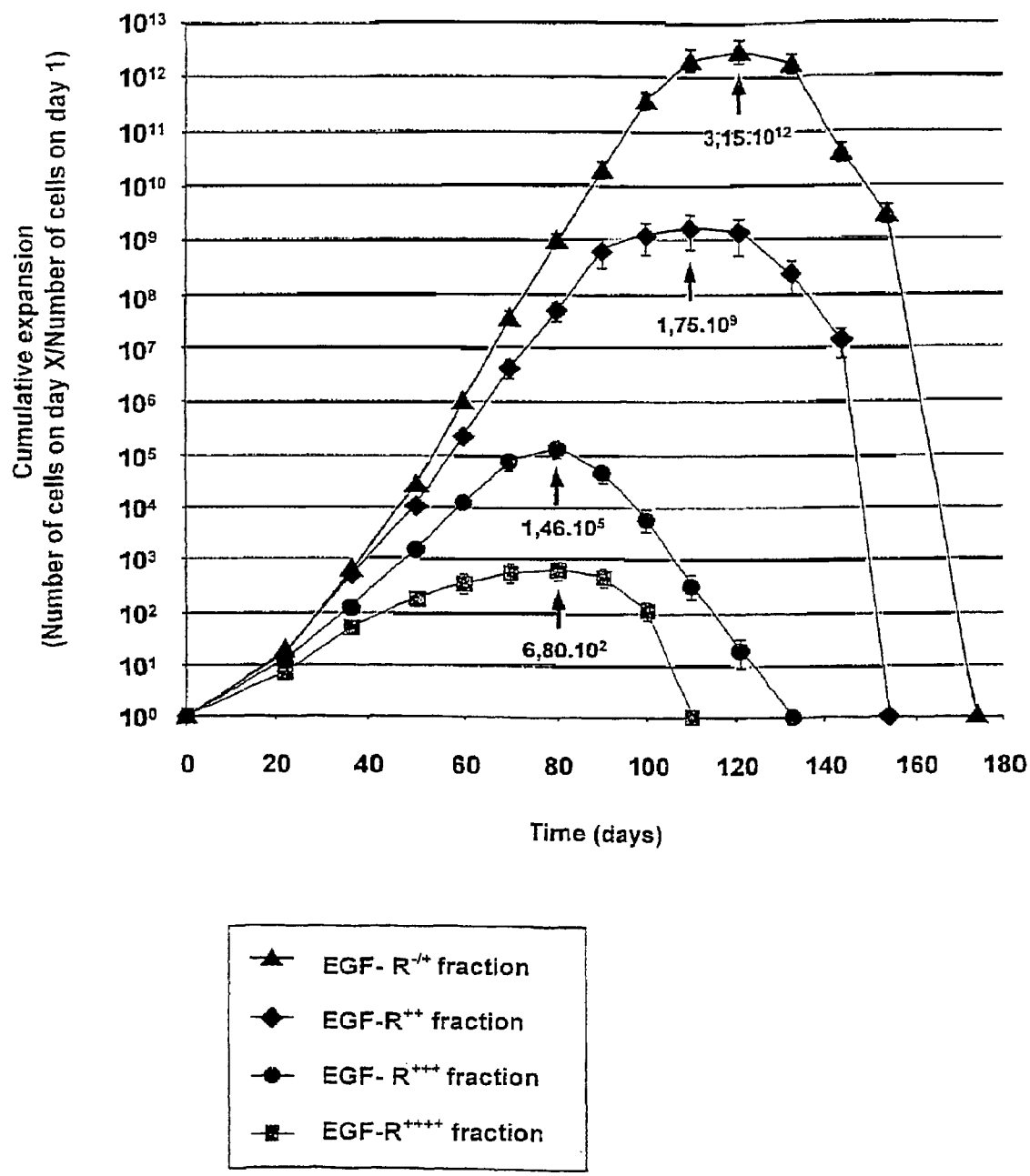
FIG. 7 shows a comparison of the long-term expansion potential of the keratinocytes contained in fractions EGF-$R^{-/+}$EGF-$R^{++}$, EGF-$R^{+++}$, and EGF-$R^{++++}$ phenotype.

FIG. 6: Separation of the population of "adherent" keratinocytes into 4 fractions on the basis of the level of expression of the EGF-R.

Keratinocytes of the population called "adherent", pre-enriched in primitive cells by a stage of adhesion on type I collagen, were marked by a fluorescent antibody directed against the EGF-R (antibody directed against the extracellular domain of the EGF-R). The signal was analyzed in a semi-quantitative manner by flow cytometry.

The x-axis represents the intensity of fluorescence measured by flow cytometry and expressed on a logarithmic scale. The y-axis represents the distribution of the cells analyzed as a function of the intensity of the fluorescent signal measured.

The flow cytometry profile presented illustrates a separation of the adherent population into 4 fractions: the fractions called "EGF-R$^{-/+}$" and "EGF-R$^{++}$" are included in the EGF-R$^{low}$ fraction and each contain 20% of the cells of the adherent population; the fractions called "EGF-R$^{+++}$" and "EGF-R$^{++++}$" are included in the fraction EGF-R$^{high}$ and each contain 20% of the cells of the population of adherent cells.

FIG. 7: Comparison of the long-term expansion potential of the keratinocytes contained in the fractions of "EGF-R$^{-/+}$", "EGF-R$^{++}$", "EGF-R$^{+++}$", and "EGF-R$^{++++}$" phenotype.

The total keratinocytes isolated from a skin sample were pre-enriched in primitive cells by the method of adhesion on type I collagen, then separated into 4 fractions: 2 extreme fractions containing respectively 20% of the cells expressing the EGF-R, "EGF-R$^{-/+}$" and "EGF-R$^{++++}$" most weakly and strongly, as well as 2 fractions having intermediate "EGF-R$^{++}$" and "EGF-R$^{+++}$" markings. The long-term expansion potential of these 4 fractions was compared (cumulative total number of cells produced).

The curve with black triangles corresponds to the results obtained from the cells of the EGF-R$^{-/+}$ fraction, that with diamonds from the cells of the EGF-R$^{++}$ fraction, that with circles from the cells of the EGF-R$^{+++}$ fraction, that with squares from the cells of the EGF-R$^{++++}$ fraction.

The results obtained show that the cell fraction called "EGF-R$^{-/+}$" is the most enriched in primitive cells having a high long-term expansion potential.

FIGS. 8A, 8B, 8C and 8D: Ability of the Adh$^{+++}$EGF-R$^{low}$ primitive cells to generate in vitro a pluristratifled epidermis.

The culture substrate used is a devitalized human dermis free from epidermis, prepared according to the method described by Regnier et al., (1981) (10). The keratinocytes originating from the different ADh$^{+++}$EGF-R$^{high}$ (4 or 7 successive culture passages) or Adh$^{+++}$EGF-R$^{low}$ (4 or 7 successive culture passages) sub-populations, were applied to this dermal substrate and cultured for 6 days in DMEM/Ham F12 medium (Invitrogen), containing 10% of foetal calf serum (Invitrogen); 10 ng/ml of EGF (BD Biosciences, USA); 0.4 µg/ml of hydrocortisone (Sigma Chemical Co); 10$^{-6}$ M of isoproterenol (Sigma Chemical Co.); 5 µg/ml of transferrin (Sigma Chemical Co.); 2×10$^{-9}$ M of triiodothyronine (Sigma Chemical Co.); 1.8×10$^4$ M of adenine (Sigma Chemical Co.), and 5 µg/ml of insulin (Sigma Chemical Co.). The cultures were then placed at the air-liquid interface and continued in the absence of isoproterenol, transferrin, triiothyronine and adenine. The histological analysis of the reconstructed epidermes was carried out 7 days later. (N.B. Adh$^{+++}$ indicates keratinocytes originating from the adherent population following pre-enrichment).

FIG. 8A shows a microscopic cross-section corresponding to an epidermis generated from Adh$^{+++}$EGF-R$^{low}$ keratinocytes at passage 4. The epidermis obtained is correctly formed and differentiated. The scale represented, of maximum size 100 µm, is graduated every 10 µm.

FIG. 8B shows a microscopic cross-section corresponding to an epidermis generated from Adh$^{+++}$EGF-R$^{high}$ keratinocytes at passage 4. The epidermis obtained is correctly formed and differentiated. The scale represented, of maximum size 100 µm, is graduated every 10 µm.

FIG. 8C shows a microscopic cross-section corresponding to an epidermis generated from Adh$^{+++}$EGF-R$^{low}$ keratinocytes at passage 7. The epidermis obtained is correctly formed and differentiated. The scale represented, of maximum size 100 µm, is graduated every 10 µm.

FIG. 8D shows a microscopic cross-section corresponding to an epidermis generated from Adh$^{+++}$EGF-R$^{high}$ keratinocytes at passage 7. The epidermis obtained is degenerative. The scale represented, of maximum size 100 µm, is graduated every 10 µm.

The results show that the organogenic potential of the Adh$^{+++}$EGF-R$^{low}$ sub-population is more durable than that of the keratinocytes of the Adh$^{+++}$EGF-R$^{high}$ sub-population.

FIGS. 9A, 9B and 9C: phenotyping by flow cytometry of the non-fractionated population of keratinocytes and of the adherent and non-adherent fractions obtained after pre-enrichment.

Immuno-phenotypical markings are carried out on samples of 50,000 cells in suspension in PBS/BSA at 0.2%. In order to limit the non-specific binding of antibodies, the cells are firstly incubated in the presence of "gamma globulins" originating from the same species as the antibodies used for the markings (Rat γ globulin or Mouse γ globulin, Jackson ImmunoResearch Laboratories Inc., Immunotech, Marseille, France) for 10 minutes at 4° C. The cells are then incubated for 30 minutes at 4° C. in the presence of an anti-CD49f-FITC antibody (α6 chain integrin) produced in rats (marking) (anti-human CD49f-FITC rat IgG$_{2a}$; GoH3 clone, Pharmingen, San Diego, Calif., USA) or a control non-specific antibody of the same isotype (isotypic control) (rat IgG$_{2a}$-FITC isotypic control, Dako, Glostrup, Denmark); an anti-CD49b-PE antibody (α2 chain integrin) produced in mice (marking) (anti-human CD49b-PE mouse IgG$_{2a}$; 12F1-H6 clone, Pharmingen, San Diego, Calif., USA) or a control non-specific antibody of the same isotype (isotypic control) (mouse IgG$_{2a}$-PE isotypic control; G155-178 clone, Pharmingen, San Diego, Calif., USA); an anti-CD29-PE antibody (β1 chain integrin) produced in mice (marking) (anti-human CD29-FITC mouse IgG$_1$; 4B4 clone, Coulter Corp., Miami, Fla., USA) or a control non-specific antibody of the same isotype (isotypic control) (mouse IgG$_1$-FITC isotypic control; Becton Dickinson, San Jose, Calif., USA). The cells are then washed in PBS/BSA before being analyzed by flow cytometry. For each sample, the statistics are based on at least 10,000 events taken into account.

FIG. 9 represents the percentage (y-axis) of cells of the non-fractionated population (before passage on collagen, white column), the adherent population (12 minutes on type I collagen, black column) and the non-adherent population (12 minutes on type I collagen, grey column) positive to the immunological marking of the α6, α2 and β1 integrins. These results are the averages and standard deviations obtained for 3 independent experiments.

FIG. 9A shows the percentage (y-axis) of cells of the non-fractionated population (white column), the adherent population (12 minutes on type I collagen, black column) and the non-adherent population (12 minutes on type I collagen, grey column) positive to the immunological marking of the α6 integrin.

FIG. 9B shows the percentage (y-axis) of cells of the non-fractionated population (white column), the adherent population (12 minutes on type I collagen, black column) and the non-adherent population (12 minutes on type I collagen, grey column) positive to the immunological marking of the α2 integrin.

FIG. 9C shows the percentage (y-axis) of cells of the non-fractionated population (white column), the adherent population (12 minutes on type I collagen, column noire) and the non-adherent population (12 minutes on type I collagen, grey column) positive to the immunological marking of the β1 integrin.

The results show that approximately 70% of the cells of the population of adherent cells express the α6 integrin whilst approximately 40% of the cells of the non-fractionated population express this integrin and only approximately 30% of the cells of the non-adherent population express it.

EXAMPLES

I/Isolation of the Keratinocytes from a Skin Sample (Prepuce)

After elimination of the sub-cutaneous tissue using a scalpel, the skin sample is cut up into fragments of approximately 5 mm×5 mm, then decontaminated by an antibiotic treatment (Gentamycin (Life Technologies Ltd, Paisley, Scotland), 3 successive 10-minute baths in DMEM culture medium (Life Technologies Ltd, Scotland)). In order to allow the separation of the dermis from the epidermis, the sample is then subjected to a proteolytic treatment (dispase (Boehringer, Roche Diagnostics GmbH, Mannheim, Germany) overnight at 4° C., then 30 minutes at 37° C.). The fragments of epidermis separated from the dermal tissue are placed in a 0.05% trypsin-0.02% EDTA solution (Biological Industries, Kibbutz Beit Haemek, Israel) (15 minutes at 37° C.). The preparation is stirred periodically in order to promote the dissociation of the cells. The effect of the trypsin is then neutralized by the addition of a culture medium containing 10% foetal calf serum (FCS) (Sigma-Aldrich, St Quentin Fallavier, France) (DMEM+10%FCS). The cell suspension is homogenized, then washed in keratinocyte culture medium (Keratinocyte growth medium, KGM) (KGM Bullet Kit, BioWhittaker, Clonetics Corp., San Diego, Calif., USA). The cells in suspension are counted with a microscope using a Malassez cell. The viability of the samples is estimated by the method of exclusion with Trypan blue (Life Technology, Cergy Pontoise Cedex, France).

II/Enrichment of a Preparation of Keratinocytes in Primitive Cells from the Basal Layer of the Epidermis The basal layer of the epidermis contains the most primitive keratinocytes called "stem cells". These cells can be separated from the more mature keratinocytes on the basis of their rapid adhesion property. This stage allows a pre-enrichment of the preparation in primitive cells.

The cell suspension is placed in culture flasks "covered" with type I collagen (solution of collagen I (Sigma Chemical Co Ltd, Irvine, UK) diluted by a factor of 2 in PBS, applied to the flasks over 45 minutes, followed by drying after elimination of the surplus), at a density of 200,000 cells/cm$^2$. After 12 minutes, the keratinocytes not having adhered are eliminated by washing in PBS buffer. The adherent cells thus selected are detached from the support by a mild trypsinization (0.05% trypsin-0.02% EDTA (Biological Industries, Kibbutz Beit Haemek, Israel) for 3 to 5 minutes at 37° C.). After neutralization of the trypsin (DMEM+10% FCS), the cells are recovered, washed, then resuspended in KGM medium. The fraction of the adherent cells selected by this method represents approximately 10% of the total keratinocytes of the epidermis.

III/Short Term Clonogenic Tests

The keratinocytes are cultured in KGM medium at a low density (1600, 3200 and/or 4800 cells/cm$^2$) in order to obtain well individualized clones which are easily observable with a microscope. The culture medium is renewed 3 times per week until the experiments are stopped (6 to 12 days). The clones are then fixed and stained, then counted and classified according to the number of cells which compose them.

For staining, the preparations are firstly fixed for 30 minutes at ambient temperature with formalin (formaldehyde in 35% solution) (Merck, Darmstadt, Germany) diluted to 10% in PBS buffer (BioWhittaker Inc., Walkersville, Mass., USA), then washed twice with water. The cells are then incubated for 2 minutes with filtered hematoxylin (staining of the nuclei) (Sigma diagnostics, St Louis, Mo., USA). After rinsing with water, the preparations are dried in air, then incubated for 5 minutes in 1% eosin (Sigma diagnostics, St Louis, Mo., USA) in PBS buffer. They are again washed with water, then dried.

IV/Phenotyping by Flow Cytometry of the Non-Fractionated Population of Keratinocytes, of the Adherent and Non-Adherent Fractions Obtained after the Pre-Enrichment Immuno-phenotype markings are carried out on samples of 50,000 cells in suspension in PBS/BSA at 0.2%. In order to limit the non-specific binding of antibodies, the cells are firstly incubated in the presence of "gamma globulins" originating from the same species as the antibodies used for the markings (Rat γ globulin or Mouse γ globulin, Jackson ImmunoResearch Laboratories Inc., Immunotech, Marseille, France) for 10 minutes at 4° C. The cells are then incubated for 30 minutes at 4° C. in the presence of an anti-CD49f-FITC antibody (α6 chain integrin) produced in rats (marking) (anti-human CD49f-FITC rat IgG$_{2a}$; GoH3 clone, Pharmingen, San Diego, Calif., USA) or a control non-specific antibody of the same isotype (isotypic control) (rat IgG$_{2a}$-FITC isotypic control, Dako, Glostrup, Denmark); an anti-CD49b-PE antibody (α2 chain integrin) produced in mice (marking) (anti-human CD49b-PE mouse IgG$_{2a}$; 12F1-H6 clone, Pharmingen, San Diego, Calif., USA) or a control non-specific antibody of the same isotype (isotypic control) (mouse IgG$_{2a}$-PE isotypic control; G155-178 clone, Pharmingen, San Diego, Calif., USA); an anti-CD29-PE antibody (β1 chain integrin) produced in mice (marking) (anti-human CD29-FITC mouse IgG$_1$; 4B4 clone, Coulter Corp., Miami, Fla., USA) or a control non-specific antibody of the same isotype (isotypic control) (mouse IgG$_1$-FITC isotypic control; Becton Dickinson, San Jose, Calif., USA). The cells are then washed in PBS/BSA before being analyzed by flow cytometry. For each sample, the statistics are based on at least 10,000 events taken into account.

The results presented in FIG. 9 indicate that the population of adherent cells on the type I collagen frequently express the α6 integrin (approximately 70% of the positive cells) relative to the non-fractionated population (approximately 40% of the positive cells) and the non-adherent population (approximately 30% of the positive cells). The population of adherent cells therefore has a significant enrichment in α6-type integrins relative to the non-fractionated population. By comparison, the α2 and β1 integrins are not markers suitable for the evaluation of the enrichment obtained as the majority of the cells of the three populations (non-fractionated, adherent, non-adherent) express these integrins.

V/Marking of the EGF Receptor (EGF-R) for Analysis and Screening by Flow Cytometry The cells in suspension are centrifuged and taken up in PBS buffer containing 0.2% of bovine serum albumin (BSA) (Sigma Chemical Co., St Louis, Mo., USA) (PBS/0.2% BSA). In order to limit the non-specific binding of antibodies, the cells are firstly incubated in the presence of "rat gamma globulins" (Rat γ globulin, Jackson ImmunoResearch Laboratories Inc., Immunotech, Marseille, France) for 10 minutes at 4° C. The cells are then incubated for 30 minutes at 4° C. in the presence of a non-conjugated anti-EGF-R antibody (extracellular domain) produced in mice (marking) (anti-human EGF-R mouse $IgG_{2b}$; EGFR1 clone, Dako, Glostrup, Denmark) or a control non-specific antibody of the same isotype as the anti-EGF-R antibody (isotypic control) (mouse $IgG_{2b}$ isotypic control, Immunotech, Marseille, France). After 2 successive washings in PBS/0.2% BSA, the cells are incubated in the presence of a secondary antibody produced in rats and coupled with phycoerythrin (PE), capable of recognizing the mouse antibodies (Rat anti-Mouse $IgG_{2a+b}$-PE, Becton Dickinson, San Jose, Calif., USA) (30 minutes at 4° C.). The cells are again washed twice, before being used for screening by flow cytometry (FACS Vantage, Becton Dickinson, San Jose, Calf., USA).

The population of adherent keratinocytes was separated into fractions having different levels of expression of the EGF-R and the cells that they contain screened in order to characterize them from a functional point of view.

VI/Evaluation of the Long-Term Expansion Potential of the Fractions of Keratinocytes Screened by Flow Cytometry The cells of each sub-population, screened by flow cytometry, are subjected to a functional test making it possible to evaluate their long-term expansion ability (property associated with the most primitive cells called "stem cells").

After estimation of the viability by the method of exclusion with Trypan blue, 60,000 cells of each sub-population are seeded in non-"covered" culture flasks, with a surface area of 25 cm². The culture medium (KGM) is changed 3 times per week. The cells are detached from their support, counted and reseeded at a rate of 60,000 viable cells per 25 cm² flask when the cultures reach 70-80% confluence, in order to avoid the cells becoming committed to differentiation following the contact inhibition phenomena. The detachment of the cells is carried out in 2 successive stages. The first is mild trypsinization (0.05% trypsin-0.02% EDTA (Biological Industries, Kibbutz Beit Haemek, Israel) for 3 to 5 minutes at 37° C.) which makes it possible to detach approximately 80% of the cells. The cells which are more difficult to detach for which mild proteolysis has proved ineffective are then subjected to stronger trypsinization (0.25% trypsin-0.02% EDTA (Biological Industries, Kibbutz Beit Haemek, Israel) for 5 minutes at 37° C.) which makes it possible to recover all of the cell population.

At each passage, the cumulative expansion obtained is calculated for each culture (number of cells produced on day X/number of cells seeded on day 1). The experiments are continued until the cell proliferation potential is exhausted. The results are shown in the form of a cumulative expansion curve which makes it possible to visualize the total proliferation potential of each of the cell sub-populations tested.

VII/Ability of the Epidermal Stem Cells Selected to Generate a Reconstructed Epidermis in Vitro Another characteristic of the $Adh^{+++}EGF-R^{low}$ keratinocytes which was evaluated is their organogenic potential, i.e. their ability to generate in vitro a pluristratified epidermis (N.B. $Adh^{+++}$ means keratinocytes originating from the adherent population following pre-enrichment). Keratinocytes of the $Adh^{+++}EGF-R^{high}$ and $Adh^{+++}EGF-R^{low}$ sub-populations were cultured during 7 successive passages. At each passage, some of the amplified cells were sampled in order to be seeded on a dermal substrate. In the early passages (passage 4), the keratinocytes originating from the cultures initiated with $Adh^{+++}EGF-R^{high}$ cells and with $Adh^{+++}EGF-R^{low}$ cells have showed a good ability to produce a good-quality epidermis (FIG. 8A, FIG. 8B). In both cases, the histology is characteristic of a correctly formed and differentiated epidermis: I) a basal layer containing polygonal cells orientated perpendicularly to the dermal substrate, II) 3 to 4 layers of spiny cells, III) 4 to 6 layers of granular cells, and IV) a compact stratum corneum comprising anucleated horn cells. At a higher number of passages (passage 7), it was observed that only the keratinocytes originating from the $Adh^{+++}EGF-R^{low}$ sub-population remain capable of generating an epidermis (FIG. 8C), the cultures originating from the $Adh^{+++}EGF-R^{high}$ sub-population producing no more than a degenerative epidermis (FIG. 8D). These results demonstrate the organogenic potential of the $Adh^{+++}EGF-R^{low}$ sub-population which is more durable than that of the keratinocytes of the $Adh^{+++}EGF-R^{high}$ sub-population.

REFERENCES

1. Aumailley M & T Krieg (1996). Laminins: a family of diverse multifunctional molecules of basement membranes. *J Invest Dermatol*. 106: 209-214.
2. Clark R A (1990). Fibronectin matrix deposition and fibronectin receptor expression in healing and normal skin. *J Invest Dermatol*. 94: 128-134.
3. Couchman J R, Austria M R & A Wood (1990). Fibronectin-cell interactions. *J Invest Dermatol*. 94: 7-14.
4. Couchman J R (1993). Hair follicle proteoglycans. *J Invest Dermatol*. 101: 60-64.
5. Mc Grath J A & R A Eady (1997). Heparan sulphate proteoglycan and wound healing in skin. *J Pathol*. 183: 264-271.
6. Sage H (1982). Collagens of basements membranes. *J Invest Dermatol*. 79: 51-59.
7. Uitto J & L Pulkkinen (1996). Molecular complexity of the cutaneous basement membrane zone. *Mol Biol Rep*. 23: 35-46.
8. Allison D C & P Ridolpho (1980). Use of a trypan blue assay to measure the deoxyribonucleic acid content and radioactive labeling of viable cells. *J Histochem Cytochem*. 28: 700-703.

9. Barrandon Y & H Green (1985). Cell size as a determinant of the clone-forming ability of human keratinocytes. *Proc Natl Acad Sci USA*. 82: 5390-5394.

10. Regnier M, Prunieras M & D Woodley (1981). Growth and differentiation of adult epidermal cells on dermal substrates. *Front. Matrix Biol.* 9: 4-35.

The invention claimed is:

1. A method for enriching keratinocyte stem cells (KSCs) from a sample of keratinocytes and KSCs, said KSCs having an expansion potential of at least $10^9$ after about 100 days in culture, comprising:
   (a) providing a sample of keratinocytes and KSCs;
   (b) contacting said sample with a culture plate coated with collagen for approximately 12 minutes; and then
   (c) washing away non-adherent cells; and then
   (d) recovering adherent cells; and then
   (e) sorting the recovered adherent cells by their expression level of EGFR; and then
   (f) recovering the cells whose expression level of EGFR is less than about 50% of the maximum level of EGFR expression in said recovered adherent cells,
   wherein the cells recovered in step (f) are KSCs and wherein said KSCs have an expansion potential of at least $10^9$ after about 100 days in culture.

2. The method of claim 1, wherein the EGFR expression level in the population of keratinocyte stem cells is between about 2% and about 5% of the maximum level of EGFR expression in said population of cells.

* * * * *